United States Patent [19]
Moulton-Barrett et al.

[11] Patent Number: 5,542,419
[45] Date of Patent: Aug. 6, 1996

[54] **NONINVASIVE METHOD TO DETECT GASTRIC *HELICOBACTER PYLORI***

[75] Inventors: Rex Moulton-Barrett, Irvine, Calif.; Robert Michener, Boston, Mass.

[73] Assignee: Boston University, Boston, Mass.

[21] Appl. No.: 202,969

[22] Filed: Feb. 28, 1994

[51] Int. Cl.$^6$ .................................................... A61B 5/08
[52] U.S. Cl. .................................................... 128/630
[58] Field of Search .................................... 128/630, 760, 128/763, 719, 716, 897, 898

[56] References Cited

U.S. PATENT DOCUMENTS

| | | | |
|---|---|---|---|
| 4,947,861 | 8/1990 | Hamilton | 128/898 |
| 5,233,997 | 8/1993 | Klein et al. | 128/898 |
| 5,262,156 | 11/1993 | Alemohammand | 424/92 |
| 5,386,832 | 2/1995 | Wagner et al. | 128/898 |

OTHER PUBLICATIONS

Kroopnick, P., *Deep Sea Res.*, 21:211–227 (1974).
Coleman, D. C. and Corbin, F. T., *Carbon Isotope Tech.*, (1991).
Moulton–Barret, R. et al., *Am. J Gastroenterol.*, 88(3):369–374 (1993).
Hentschel, E. et al., *New Eng. J. Med.*, 328(5):308–312 (1993).
Graham, D. Y., *New Eng. J. Med.*, 328(5):349–350 (1993).
Graham, D. Y. et al., *Ann. Int. Med.*, 116(9):705–708 (1992).
Monmaney, T., *New Yorker*, (Sep. 20, 1993).

*Primary Examiner*—Angela D. Sykes
*Assistant Examiner*—Samuel Gilbert
*Attorney, Agent, or Firm*—Baler & Botts, L.L.P.; Patrick Turley

[57] ABSTRACT

The present invention provides a method for measuring dissolved inorganic carbon (DIC) in body fluids. The method can be used to measure DIC in blood, serum, plasma, urine, sweat, saliva, lacrimal fluid, and combinations thereof. The method can be used to diagnose a gastrointestinal disorder in a subject, and particularly a gastrointestinal disorder mediated by a urease producing bacterium such as *Helicobacter priori*.

6 Claims, 2 Drawing Sheets

NONINVASIVE METHOD TO DETECT GASTRIC *HELICOBACTER PYLORI*

BACKGROUND OF THE INVENTION

1. Field of the Invention

The present invention relates to a method for diagnosing gastrointestinal disorders. The invention also relates to a method for measuring dissolved inorganic carbon (DIC) in biological fluids.

2. Description of the Prior Art

Among the chronic disorders of the upper gastrointestinal tract are those which fall under the general categories of gastritis and peptic ulcer disease. The upper gastrointestinal tract is generally defined as including the esophagus, the stomach, the duodenum, the jejunum, and the ileum. Peptic ulcers are lesions of the gastrointestinal tract lining, characterized by loss of tissue due to the action of digestive acids and pepsin. It has been generally held that peptic ulcers are caused by gastric hypersecretion, decreased resistance of the gastric lining to digestive acids and pepsin, or both. Gastritis is, by definition, an inflammation of the stomach mucosa. In practice, though, the disorder is manifested by a broad range of poorly-defined, and heretofore inadequately treated symptoms such as indigestion, "heartburn", dyspepsia and excessive eructation.

*Helicobacter pylori* (HP) is a curved Gram-negative rod which colonizes gastric mucosa and is etiologically associated with histologic gastritis. HP has been isolated from gastric mucosa by histology and culture in 25 to 36% of asymptomatic populations, in 83% of persons with duodenal ulceration, and in 77 to 100% of patients with chronic active gastritis. Diagnosis of HP infection has traditionally been made by endoscopy and biopsy.

Because the most distinctive characteristic of HP is the production of highly active urease, urease tests and urea breath tests have been increasingly utilized recently for the diagnosis of HP infection. The CLOtest, such as described by Morris, A., et al., *Lancet,* 1:149 (1986), is a commercially available test for the colormetric detection of urease activity in endoscopic biopsy specimens.

Diagnosis of t IP infection may also be conducted by IgG or IgA antibody serology as described by Evans, DJ. et al., *Gastroenterology,* 96:1004- 8 (1989). Serologic screening for IgG or IgA antibodies to HP does not provide reliable information because antibody titers against HP tend to fall slowly over several months after successful antibacterial therapy, and generally remain in the abnormal range after therapy.

Diagnosis may also be made by the $CO_2$ breath test as described in U.S. Pat. No. 4,830,010. The breath test is conducted by administering urea to a subject and measuring $CO_2$ released. The urea may be isotope-labeled with $^{13}C$ or $^{14}C$. Urease catalyzes the release of $CO_2$ from urea. $CO_2$ released from urea by urease may be found in several dissolved inorganic carbon (DIC) forms in tissues. These DIC forms are carbonate ($CO_3^=$), bicarbonate ($HCO3^-$), carbonic acid ($H_2CO_3$) and dissolved $CO_2$. Although the $CO_2$ breath test provides a noninvasive form of diagnosing HP infection, the method requires specialized collection and transportation apparatus, usually requires 50 cc of exhalate, and is time consuming. When $^{14}C$ is used, the $CO_2$ breath test necessitates a small amount of radiation, which precludes its use in pregnant women and small children.

A method for measuring DIC in body fluid samples has not heretofore been described. Current methods for measuring forms of DIC include physical techniques such as Natelson microgasometry and enzymatic methods based on phosphoenolpyruvate carboxylase (for measuring bicarbonate). These methods are unsuitable for detecting DIC elevations in body fluids caused by bacterial urease activity. Thus far, extraction of blood $^{13}C$-bicarbonate had been difficult because, upon contact with a mineral acid, blood coagulates and impedes the liberation of $CO_2$ from the sample.

These and other disadvantages of the prior art are overcome by the present invention, and a new method for measuring DIC and for diagnosing or monitoring gastrointestinal disorders is provided.

SUMMARY OF THE INVENTION

It is an object of the present invention to provide a method for measuring DIC in body fluids.

It is a further object of the present invention to provide a method for diagnosing or monitoring a gastrointestinal disorder in a subject.

Accordingly, the present invention provides a method for diagnosing in a subject a gastrointestinal disorder of the upper gastrointestinal tract caused or mediated by bacteria, said method comprising measuring isotope-labeled dissolved inorganic carbon in at least one body fluid of said subject.

The present invention also provides a method for diagnosing in a subject a gastrointestinal disorder of the upper gastrointestinal tract caused or mediated by bacteria, said method comprising the steps of administering to said subject isotope-labeled urea, and analyzing at least one body fluid of said subject for the presence of isotope-labeled dissolved inorganic carbon.

The present invention also provides a method for diagnosing in a subject an infection of bacteria that cause or mediate at least one gastrointestinal disorder, wherein said bacteria are characterized by the ability to convert at least one organic carbon source to at least one absorbable dissolved inorganic carbon compound, said method comprising administering to said subject at least one labeled organic carbon source, collecting at least one sample of at least one body fluid from said subject, liberating $CO_2$ gas from said at least one sample, and analyzing said $CO_2$ gas for at least one labeled species to diagnose infection of bacteria that cause or mediate at least one gastrointestinal disorder.

The present invention also provides a method for determining the amount of labeled dissolved inorganic carbon in a body fluid of a subject, said method comprising the steps of administrating at least one labeled organic carbon source to said subject; collecting at least one sample of at least one body fluid from said subject; liberating $CO_2$ gas from said at least one sample; and analyzing said $CO_2$ gas for labeled species to determine the amount of labeled dissolved inorganic carbon.

The present invention also provides a kit for determining labeled dissolved inorganic carbon, said kit comprising at least one labeled carbon source, and at least one preevacuated specimen collection container.

These and other advantages of the present invention will become apparent from the following detailed description.

DETAILED DESCRIPTION OF THE INVENTION

Figure 1:
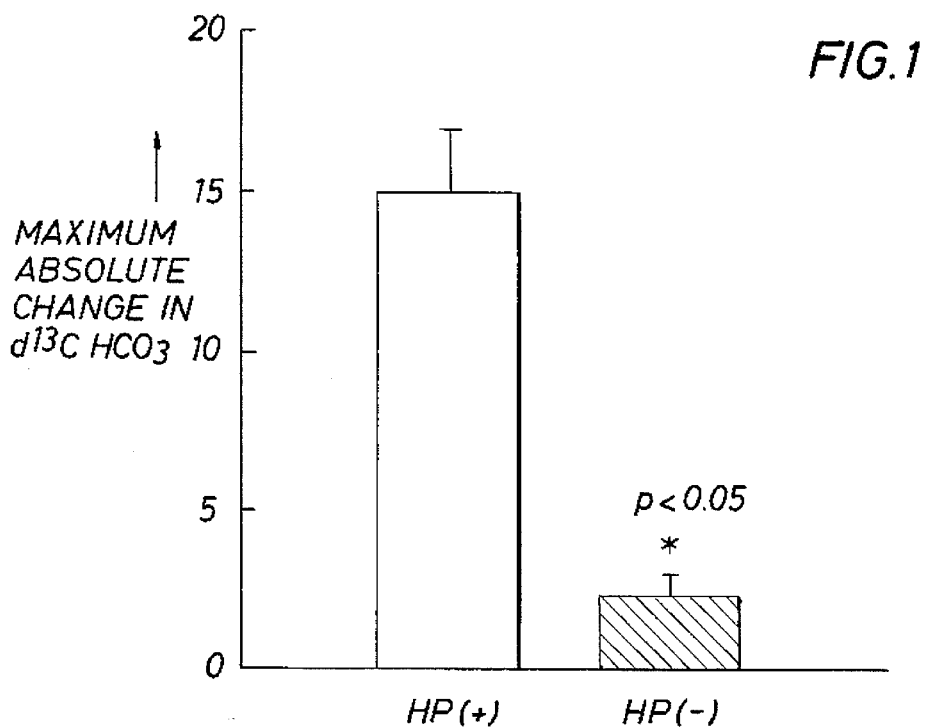
FIG. 1 shows the results of mass spectrometric analysis from HP(+) and HP(−) subjects.

The present invention provides a method for the diagnosis of a gastrointestinal disorder in a human or lower animal subject, comprising the steps of administering a safe and effective amount of urea to the subject and analyzing the body fluid(s) of the subject for the presence of DIC hydrolysis products of the administered urea. The presence of the products of hydrolysis is a positive indication of a gastrointestinal disorder in the test subject.

As used herein, "gastrointestinal disorder" includes, but is not limited to, any disease or other disorder of the gastrointestinal tract of a human or lower animal. Such gastrointestinal disorders include, for example: disorders not manifested by presence of ulcerations in the gastric mucosa (herein "nonulcerative gastrointestinal disorder"), including chronic or atrophic gastritis, gastroenteritis, nonulcer dyspepsia, esophageal reflux disease and gastric motility disorders; gastric carcinomas and "peptic ulcer disease", i.e., gastric and duodenal ulcers. In particular, "gastrointestinal disorder" refers to such disorders of the upper gastrointestinal tract caused or mediated by bacteria, including HP.

The present invention also provides methods for diagnosing disorders caused or mediated by microorganisms having high urease activity. Such microorganisms include, but are not limited to HP, and Proteus species such as, but not limited to *Proteus mirabilis, Proteus morganii, Proteus rettgeni,* and *Proteus vulgaris*.

In one embodiment of the present invention a "background" body fluid sample is collected shortly before or during administration of urea to the subject. If the sample is collected before administration of urea, it should be done so within a reasonable time, such as about 0.1 to about 6 hours and preferably about 0.5 to about 1.0 hours before urea is administered. In an alternative embodiment urea is administered without collecting the background sample. A safe and effective amount of urea is administered to the subject. As used herein, the term "urea" refers to urea or suitable derivatives of urea that are acted upon by urease. As used herein, the term "safe and effective amount" refers to an amount of urea that is sufficient to produce a detectable level of DIC, without undue adverse side effects (such as toxicity, irritation or allergic responses) commensurate with a reasonable risk/benefit ratio. The specific, safe, and effective amount of urea to be administered may depend upon such factors as the particular body fluid to be tested, the weight of the test subject, and (when using isotope-labeled urea) the relative amount or concentration of isotope present in the urea. A safe and effective amount of urea is typically from about 1 mg to about 20 mg of urea per kilogram of body weight of the subject.

As used herein, the terms "administering" or "administration of" urea refer to any method in accordance with good medical practice of introducing urea into the upper gastrointestinal tract of the subject. Such administration is preferably by oral ingestion of urea, in single or multiple doses. The particular dosage form used to administer the urea may be, for example, in solid tablets or capsules, or in liquid solutions or emulsions. The urea may be administered essentially in pure form, or as part of a composition.

Compositions useful in administration of urea may also contain pharmaceutically-acceptable components such as, for example, diluents, emulsifiers, binders, lubricants, colorants, flavors and sweeteners. Although urea is tasteless to most humans, it may be mixed with a delivery vehicle to make it more palatable. Suitable delivery vehicles include, but are not limited to, Sustacal or Enteral (both from Mead Johnson, Evansville, Ind.), or fruit juice. Optional components useful herein must not, however, interfere with hydrolysis of the urea or generate appreciable quantities of $CO_2$ in the upper gastrointestinal tract. A preferred optional component is one which delays gastric emptying, thereby increasing the length of time that the administered urea is present in the upper gastrointestinal tract.

In a given quantity of naturally occurring urea, the distribution of the various isotopes of carbon comprising the urea molecules is essentially identical to the broad distribution of those isotopes in nature. Accordingly, for example, the carbon atoms in a given sample of urea are predominantly $^{12}C$, with small quantities (approximately 1.1%) of $^{13}C$. $^{14}C$ isotope, which is a radioactive, unstable isotope with a half-life of approximately 5730 years, is generated by neutron bombardment of $^{13}C$. As used herein, the term "isotope-labeled" refers to a compound (urea or its hydrolysis products) having a distribution of carbon isotopes significantly different from the distribution of carbon isotopes generally occurring in nature. In methods where it is intended to analyze the body fluid of the test subject for DIC hydrolysis product of administered urea, it is particularly preferred to administer isotope-labeled urea to the subject, i.e., $^{13}C$ or $^{14}C$ isotope-labeled urea, or combinations thereof. One embodiment of this invention involves administration of from about 0.1 to about 10 microcuries of $^{14}C$-labeled urea.

Following the step of administering urea to a subject, the methods of this invention include the step of analyzing the body fluid of the subject for the presence of hydrolysis products of the administered urea.

A preferred analysis step of this invention employs detection of DIC. It is preferable to administer isotope-labeled urea to the subject. Isotope-labeled DIC as $CO_2$ is then detected as the hydrolysis product in the body fluid of the subject. After administration of the isotope-labeled urea, a period of from about 1 to about 180 minutes, preferably from about 20 to about 120 minutes, is allowed to elapse. One or more body fluid samples of the subject are then obtained for analysis. Most preferably, the sample is collected at about 60 minutes after administration of urea. The sample(s) is analyzed using the DIC method described below. In a preferred embodiment, a reference range from noninfected subjects is determined. The result of the test subject is compared to the reference range. In Example 2 following, a δ value of 6 was determined to be the cutoff. δ values above 6 were considered "positive" for HP infection. Values below 6 were "negative." Other reference range cutoffs may be used depending on age of the subject, type of label administered, etc.

DIC is measured in body fluids samples as described below. Suitable body fluids include, but are not limited to, whole blood, plasma, serum, urine, sweat, saliva, and lacrimal fluid samples. In a preferred embodiment, samples are frozen after collection. If whole blood is used, the sample should be lysed by any method known to those skilled in the art for lysing whole blood samples such as, but not limited to, freezing/thawing the sample or the addition of degassed water or a mineral acid to the sample. Lysis should be conducted in a sealed container that is able to hold a vacuum.

A suitable sample size will depend on the recovery of DIC during purification, and on the sensitivity of the analytical instrument used. Suitable sample sizes may be 0.01 ml to 3 ml, preferably 0.1 ml to 2.5 ml, and most preferably 0.5 ml to 2.0 ml.

The sample is acidified with a suitable amount of a mineral acid. A suitable amount of a mineral acid is that amount which converts bicarbonate, carbonic acid and carbonate into $CO_2$. A suitable amount of mineral acid will depend on the type and the strength of the mineral acid used. Any suitable mineral acid is acceptable, including, but not limited to, phosphoric acid, acetic acid, sulfuric acid, hydrochloric acid, and nitric acid. Carbonic acid should not be used.

The mineral acid and sample are added to a container that has been preevacuated. The container must be able to hold a vacuum. Suitable containers include, but are not limited to, Vacutainers (Becton Dickinson) and sealed test tubes. Pre-evacuation of the container is conducted by applying a suitable vacuum to the container to remove the ambient atmosphere from the container. The mineral acid and body fluid are mixed by any process known to those skilled in the art, such as, but not limited to, vortexing or shaking. This mixture is allowed to stand for a suitable period to liberate DIC as $CO_2$ from the mixture into the head space of the container. The mixture may also be occasionally mixed (such as by vortexing or shaking) to promote liberation of $CO_2$ into the headspace of the container. Liberated $CO_2$ is then purified.

Purification may be conducted by cryogenic distillation. Cryogenic distillation is the separation of gases and liquids by temperature differences. Cryogenic distillation may be performed one or more times. For example, in one embodiment, the container may be fitted to a vacuum line through a suitable fitting which maintains a seal on the container. Suitable fittings include, but are not limited to, Cajon (Macedonia, Ohio) fittings. A penetrating member extends through the fitting to allow gas (and sometimes fluid) from the container to enter the vacuum line. The vacuum line may be configured with one or more traps for purifying the $CO_2$. For example, the vacuum line may comprise a trap for freezing liquids which enter the vacuum line. The liquids may be frozen at any temperature suitable for freezing the liquid phase without causing sublimation of $CO_2$. Suitable temperatures for freezing the liquid phase are 0° C. to –90° C., preferably –20° C. to –88° C., and most preferably –83° C. to –87° C. Although it is possible to use temperatures lower than –90° C., $CO_2$ recovery and analytical precision diminish at temperatures below –90° C. A second cryogenic distillation may be used to solidify $CO_2$. Solidification of $CO_2$ promotes recovery of the gas. Although it is possible to conduct the procedure without the second distillation, the second distillation is preferred as it concentrates the $CO_2$ gas. Suitable temperatures for solidifying $CO_2$ are –100° C. to –250° C., preferably –150° C. to –225° C., and most preferably –190° C. to –200° C.

In an alternative purification embodiment, the vacuum line may be first cooled to a temperature sufficient to freeze both the $CO_2$ and the liquid phase. Suitable temperatures are –100° C. to –250° C., preferably –150° C. to –225° C., and most preferably –190° C. to –200° C. The temperature may then be increased to release the $CO_2$. In this embodiment, the temperature should not be increased above –80° C. as the frozen liquids may thaw and contaminate the analytical apparatus.

The purified $CO_2$ derived from either purification embodiment is measured in an analytical instrument by techniques known to those skilled in the art, such as, but not limited to, isotope ratio mass spectrometry.

The analytical procedure may be conducted manually or may be automated. In an automated system, the analyzer may automatically mix the mineral acid with the body fluid, collect the $CO_2$ in the headspace, purify the $CO_2$, and perform the isotope analysis. A suitable automated system includes, but is not limited to, a Gilson (Middleton, Wis.) autosampler connected to an isotope ratio mass spectrometer.

In one embodiment, the analytical result may be calculated in delta notation ("$\delta$") having units of per mil (parts per thousand): $\delta X\ (0/00) = (R_{sa} - R_{st})/R_{st} * 1000$, where X is the element (carbon), and R is the ratio of isotope to carbon ($^{13}C/^{12}C$) in the sample (sa) and standard (st). The carbon value is referenced to the international standard, PDB (Pee Dee Belemnite, a marine limestone). By convention [Craig, H., *Geochim Cosmochim Acta*, 3:53-92 (1953)], the international standard has a $\delta$ value of zero. Alternatively, the standard gas may be calibrated to secondary or tertiary standards. Suitable secondary standards, such as those available from the NIST (Gaithersburg, Md.) are NBS-20 (Solenhofen limestone), NBS-21 (Spectrographic graphite), NBS-22 (hydrocarbon oil), and NBS-19 (TS limestone).

In an alternate embodiment, the analytical result may be expressed as atom %, where:

$$atom\% = [1.1237(\delta_{sa}/100+1)]/[1+0.011237(\delta_{sa}/1000+1)]$$

and where $\delta_{sa}$ is the a $\delta$ X of the sample.

In a third embodiment, the analytical result may be expressed as atom % excess, where:

atom % excess = atom % of sample – atom % of background. "Background" is the sample collected before administration of the cocktail or labeled urea.

In an alternative embodiment, the method may be used to measure the ratio of $^{14}C$ to $^{12}C$.

Kits may be prepared to assist in administration of the labeled compound and sample collection. For example, a kit may comprise the labeled compound to be administered (e.g. labeled urea), preevacuated containers for sample collection, mailing containers, and instructions. Kits may also comprise at least one delivery vehicle.

The following examples illustrate the teachings of the present invention and are not intended as limiting the scope of the invention.

EXAMPLE 1

This example describes the DIC method.

Human subjects (19) were given 200 ml of "Sustacal" (240 kcal, Mead Johnson, Evansville, Ind.) containing 5 mg/kg body weight urea (99% $^{13}C$, MSD Isotopes, Montreal, CA) in a fashion similar to the standard protocol of Graham et al., *Lancet*, 1:1174-7 (1987), incorporated herein by reference. Blood samples (3 ml each) were obtained immediately before the meal and at 15, 30, 60, 90, 120, and 180 min afterwards via a heparinized peripheral vein cannula.

DIC was measured as follows. 2 ml of 85% phosphoric acid and 1 ml of thawed whole lysed blood collected from human subjects were injected into a preevacuated vacutainer and vortexed immediately. Samples were then allowed to stand for 2 h and were vortexed every 30 min to liberate $CO_2$ trapped in solution. Liberated $CO_2$ in the headspace was then cryogenically distilled by three consecutive 5-min collections. Isolated $CO_2$ was purified using a glass vacuum line with two U-shaped tube traps: the first was a dry ice-ethanol slush which removed water, the second was liquid nitrogen which collected $CO_2$. Recovery using standard bicarbonate solutions was better than 90% at 2 h. Because each sample was analyzed separately in a disposable vacutainer, cross-contamination problems were eliminated and samples were run semiautomatically in a batch. The purified $CO_2$ was then introduced into the mass spectrometer. The $CO_2$ gas samples were analyzed on a Finnigan Delta-S isotope ratio mass spectrometer which measured the ratio of the heavy and light isotopes in a sample and compared it to a standard gas. DIC was calculated in delta notation ("δ") having units per mil (parts per thousand): $\delta X$ (0/00) $(R_{sa} - R_{st})/R_{st} * 1000$, where X was the element carbon, and R was the ratio of $^{13}C/^{12}C$ in the sample and standard. The carbon value was referenced to an international standard, PDB (Pee Dee Belemnite, a marine limestone). By convention [Craig, H., *Geochim Cosmochim Acta*, 3:53-92 (1953)], the international standard has a value of zero. DIC replication was +0.4 δ per mil. Results as shown in Table 1 below, indicate that the method can be used to detect DIC.

EXAMPLE 2

This example describes the use of the DIC method to diagnose HP infection.

Nineteen (19) patients from whom the blood samples collected in Example 1 were studied. All were males (mean age, 63 yr; range, 34–86), who were referred for diagnostic or follow-up endoscopy by their primary care physicians because of some type of upper gastrointestinal symptom(s). Such symptoms were: epigastric pain (seven patients), heartburn (seven patients), NSAID intolerance (four patients), nausea (eight patients), vomiting (seven patients), and post-prandial or nocturnal dyspepsia (nine patients). Patients excluded from the study were those with previous gastrectomy, significant kidney or liver disease, hypercapnic obstructive lung disease, and those with history of treatment with bismuth or antibiotics over the preceding 2 months.

All patients underwent endoscopy and biopsy by a gastroenterologist who independently graded the endoscopic appearance of the stomach. The Olympus GIF-XQ-10 and GIF-XV-10 fiberoptic and videoimage endoscopes (Olympus Corporation of America, Lake Success, N.Y.) were used. Size and location of erythema, erosions, or ulcers were meticulously recorded, and the magnitude of mucosal abnormality was expressed as percentage of the entire mucosal surface visualized (0%,<25%, and >25%).

Endoscopic biopsy samples were fixed in 10% buffered formalin before staining with hematoxylin and eosin. Presence and severity of gastritis were classified by a modification of the system of Whitehead et al. [Whitehead, R., et al., *J. Clin. Pathol.*, 25:1-11 (1972)] and Hazell et al. [Hazell, S., et al., *Am. J. Gastroenterol.*, 82:297-301 (1987)], with grades 0 to 3 representing absent to severe acute or chronic gastritis, depending on the degree of neutrophilic or mononuclear cell mucosal infiltration. Specifically, grade 0 was characterized by the absence of inflammatory cells, grades 1 and 2 were characterized by occasional or confluent inflammatory cell infiltration, respectively, and grade 3 was characterized by very dense inflammatory cell infiltrate and/or gland abscesses. Histologic assessment was performed by an independent pathologist who was unaware of the clinical history or the endoscopic findings corresponding to each biopsy.

Organism identification was performed on Giemsa, Gram, and periodic acid-Schiff (PAS)-stained biopsy sections and were interpreted by an independent pathologist. HP was identified as Gram-negative, four-sheath, flagellated, and curved rods forming patchy clusters in the mucinous layer of the antral mucosa. The number of organisms was quantified as none (0), few (+1), and numerous (+2) organisms.

At least two antral mucosal biopsies were placed in a single CLOtest slide (CLOtest, TriMed Specialties, Overland Park, Kans.) indicative of intrabiopsy urease activity and were read at 2 h. Follow-up readings at 24 h were not different from those obtained at 2 h. Random pH checks were performed on biopsy forceps to confirm post-formalin rinses of the forceps and that endoscopic biopsy channels achieved neutral pH.

Labeled urea was given to the patients and blood was collected and analyzed for DIC as described in Example 1.

Patients were divided into two groups, positive and negative for HP, by both histology and CLOtest. Linear regression analysis was used to correlate serum isotope values and biopsy positivity for HP, degree of histologic gastritis, serum gastrin levels, and symptoms. Differences between HP-positive and HP-negative groups were analyzed by Student's t-test for unpaired data, with a level of significance at p less than 0.05.

On endoscopy, 14 of 19 patients had erythematous patches or streaks and prominent gastric mucosal folds; five of 14 had greater than 25% surface area involvement, three of 14 had less than 25% surface area involvement, and four patients had gastric erosion(s). Histologically, 14 of the 19 patients had evidence of gastritis; eight of 14 with features of both acute and chronic inflammation, and the remaining six with only chronic inflammation. Eleven of the 19 patients had positive CLOtest and evidence of HP by histology and Giemsa stain. The majority (eight of 11) of HP(+) patients had numerous (+2) organisms; three of 11 patients had few (+1) organisms identified. Fasting serum gastrin levels were variable (range, 42–163 pmol/L) and did not differ between HP(+) and HP(−) patients.

Preliminary mass spectrometric studies in samples from seven patients (four HP-positive and three HP-negative) collected 3 h after endoscopy/biopsy revealed no differences in total $^{13}C$-total carbon in whole lysed blood. Mass spectrometric analysis was performed in 11 HP(+) patients and eight HP(−) patients. The mean maximum change in δ in HP(+) patients was 15.3 (range, 6.7–29.9) and was significantly higher 0.05) than that seen in HP(−) patients (range, 0–5.3: mean, 2.3) as shown in Table 1 and in FIG. 1.

TABLE 1

Relationship between CLOtest, Maximum Absolute Change in δ, Serum Gastrin Levels (pmol/L), Number of HP Organisms, and Histologic Gastritis in 19 Patients Studied by Mass Spectrometry

| CLOtest | Maximum Change in δ | Gastrin | HP No. | Gastritis |
|---|---|---|---|---|
| + | 19.4 | 47 | +2 | + |
| + | 12.5 | 72 | +2 | + |
| + | 17.7 | 78 | +2 | + |
| + | 15.4 | 47 | +2 | + |
| + | 8.4 | 38 | +2 | + |
| + | 18.5 | 101 | +2 | + |
| + | 6.7 | 163 | +1 | + |

TABLE 1-continued

Relationship between CLOtest, Maximum Absolute Change in δ, Serum Gastrin Levels (pmol/L), Number of HP Organisms, and Histologic Gastritis in 19 Patients Studied by Mass Spectrometry

| CLOtest | Maximum Change in δ | Gastrin | HP No. | Gastritis |
|---|---|---|---|---|
| + | 9.6 | 42 | +2 | + |
| + | 29.9 | 111 | +1 | + |
| + | 8.4 | 61 | +1 | + |
| + | 21.7 | 49 | +2 | + |
| − | 2.1 | 55 | 0 | + |
| − | 2.6 | 100 | 0 | − |
| − | 5.3 | 63 | 0 | − |
| − | 3.2 | 122 | 0 | − |
| − | 0.4 | 43 | 0 | − |
| − | 2.6 | 99 | 0 | − |
| − | 0.0 | 132 | 0 | + |
| − | 2.2 | 111 | 0 | + |

Figure 2:
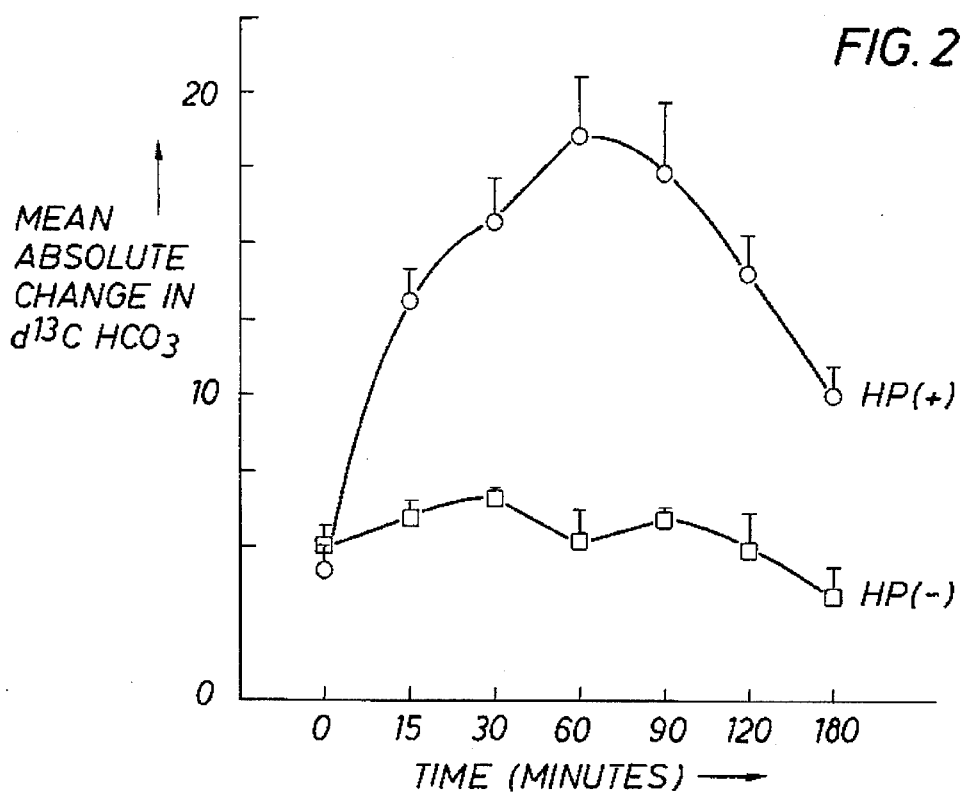
FIG. 2 shows the results of time course experiments.
Figure 3A:
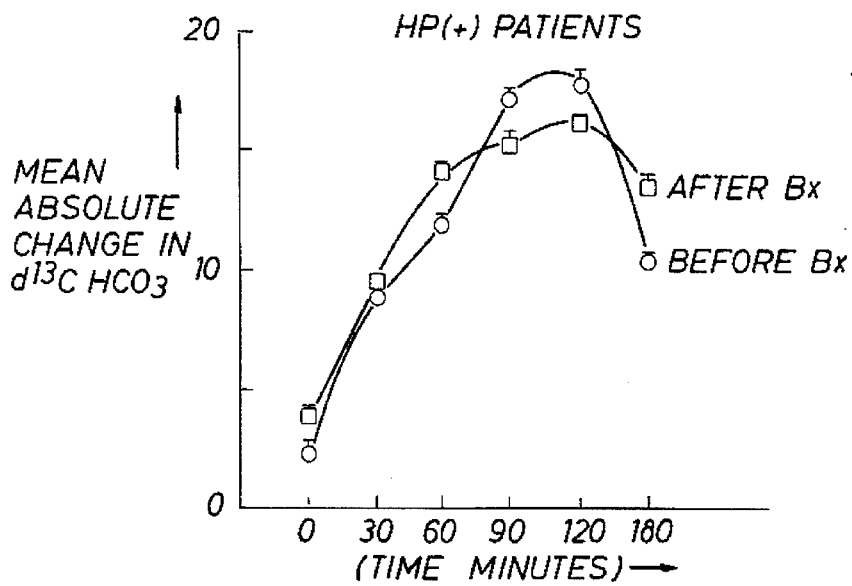
FIG. 3 shows the influence of endoscopic mucosal biopsy on DIC.
Figure 3B:
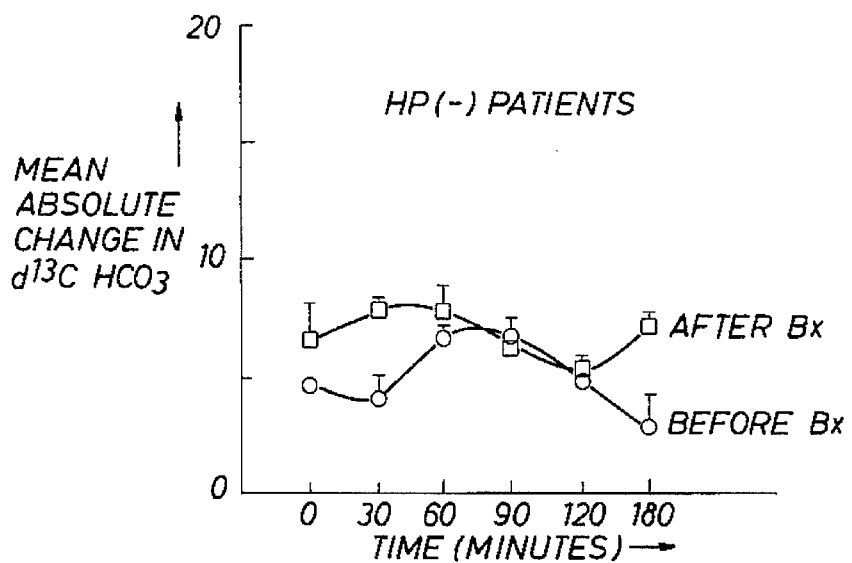

FIG. 1 shows results of mass spectrometric analysis from 11 HP(+) patients (open bar) and eight HP(−) patients (solid bar). The mean maximum change in δ was significantly higher in HP(+) than HP(−) patients. Data shown are means ±SEM (/p<0.05). Such significant increase of δ in HP(+) patients was noted at all time points tested (15–180 min), but it was maximal at 60 min after the test meal. In contrast, HP(−) patients exhibited a blunt or no increase in δ over the same time period after the test meal (FIG. 2). FIG. 2 shows the results of time-course experiments showing increase of δ after a test meal in 11 HP(+) patients (solid circles) compared with eight HP(−) patients (open circles). Data shown are means±SEM, and they are significant (p<0.05) for each time point. Furthermore, specimens could be stored for up to a period of a year without any loss of $^{13}C$ enrichment. To determine whether the performance of an endoscopic biopsy influenced these results, serial serum samples from three HP-negative and three HP-positive patients were obtained before and after endoscopic biopsy. As shown in FIG. 3, there were no differences in serum change in δ in HP-positive or HP-negative patients before and after endoscopic mucosal biopsy (FIG. 3). FIG. 3 shows the influence of endoscopic gastric mucosal biopsy (before, solid squares; after, open squares) on increase of δ after a test meal in three HP(+) patients (left panel) and in three HP(−) patients (right panel). Data shown are means±SEM, and they are not significant at any time point.

Figure 4:
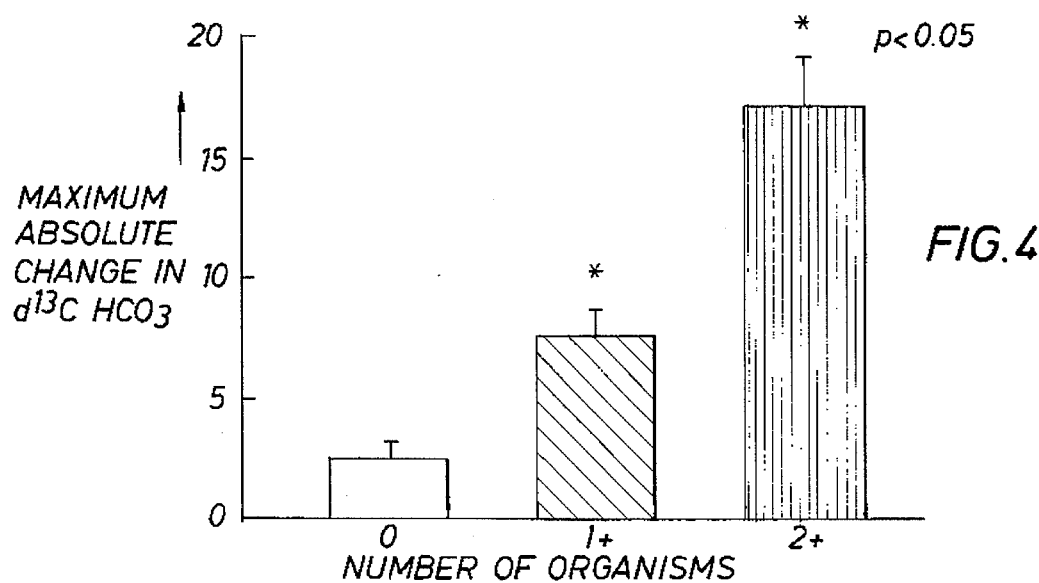
FIG. 4 shows the relationship between number of organisms and DIC.

When the maximal elevation of $^{13}C$ was compared with the number of organisms seen by histology and Giemsa stain, a significant correlation (r=0.84) was noted (FIG. 4). FIG. 4 shows the relationship between number of organisms seen by histology and Giemsa stain and maximal increase of δ after a test meal. Data shown are from 19 patients (both HP-positive and HP-negative) who underwent mass spectrometric analysis. Open bars denote means±SEM of δ in patients with no HP organisms seen; hatched bars denote means±SEM of δ from patients with few (+1) and numerous (+2) organisms, respectively. Both groups of HP(+) patients were statistically different from HP(−) patients (p<0.05). However, there was no relationship between $^{13}C$ elevation and degrees of severity of histologic gastritis, number or severity of symptoms, or serum gastrin concentrations.

Using a δ value of 6.0 at 60 min as the cutoff value between positive and negative patients, infected from non-infected patients were clearly identified. Although gastritis was seen more commonly in the HP(+) group, urea absorption—as evidenced by the total concentration of $^{13}C$ in whole lysed blood-did not change significantly during the first 3 hours in either group and, therefore, gastritis per se did not affect urea or bicarbonate absorption. In a similar fashion, the performance of endoscopic gastric mucosal biopsy did not appear to influence gastric bicarbonate absorption. Whole blood DIC elevation appears, therefore, to be due to intragastric bicarbonate generation secondary to intragastric urease activity alone.

Many other variations and modifications may be made in the techniques herein before described, by those having skill in this technology, without departing from the concept of the present invention. Accordingly, it should be clearly understood that the foregoing description is illustrative only, and not intended as a limitation on the scope of the invention.

What is claimed is:

1. A method for diagnosing in a subject an infection of bacteria, wherein said bacteria are characterized by the ability to convert at least one organic carbon source to at least one absorbable dissolved inorganic carbon compound, said method comprising administering to said subject at least one labeled organic carbon source, collecting at least one sample of a body fluid from said subject, where said body fluid is selected from the group consisting of whole blood, serum, plasma, urine, sweat, saliva, lacrimal fluid. and mucuous fluid. liberating $CO_2$ gas from said at least one sample, and analyzing said $CO_2$ gas for at least one labeled species to diagnose an infection of bacteria.

2. The method according to claim 1, wherein said administering step is administering at least one labeled organic carbon source selected from the group consisting of $^{13}C$-labeled organic carbon and $^{14}C$-labeled organic carbon.

3. The method according to claim 2, wherein said administering step is administering $^{13}C$ urea or $^{14}C$ urea.

4. The method according to claim 1, wherein said diagnosing step is diagnosing an infection of bacteria selected from the group consisting of *Helicobacter pylori, Proteus mirabilis, Proteus morganii, Proteus rettgeni* and *Proteus vulgaris*.

5. The method according to claim 1, wherein said administering step to said subject is administering at least one labelled organic carbon source to a human.

6. The method according to claim 1, wherein said administering step is administering at least one organic carbon source further comprising a pharmaceutically acceptable carrier.

* * * * *

UNITED STATES PATENT AND TRADEMARK OFFICE
CERTIFICATE OF CORRECTION

PATENT NO. : 5,542,419
DATED : August 6, 1996
INVENTOR : Moulton-Barrett, et al.

It is certified that error appears in the above-identified patent and that said Letters Patent is hereby corrected as shown below:

ABSTRACT - last word in paragraph, "priori." should read -- pylori.--.

Column 1, line 40, "colormetric" should read -- colorimetric--.

Column 1, line 42, " of t IP " should read --of HP--.

Column 1, line 57, "HCO3$^-$ " should read -- HCO$_3^-$--.

Column 6, line 31, "is the a δ" should read -- is the δ--.

Column 8, line 51, "higher 0.05) " should read -- higher (p<0.05)--.

Column 9, line 24, "±SEM (/p<0.05)" should read --±SEM (p<0.05)--.

Column 10, line 32, "where said body" should read --wherein said body--.

Signed and Sealed this

Third Day of December, 1996

*Attest:*

BRUCE LEHMAN

*Attesting Officer*   *Commissioner of Patents and Trademarks*